(12) United States Patent
Smith

(10) Patent No.: US 9,980,752 B2
(45) Date of Patent: May 29, 2018

(54) DISC AND MOTION PRESERVING IMPLANT SYSTEM

(71) Applicant: Eric J. Smith, Willoughby Hills, OH (US)

(72) Inventor: Eric J. Smith, Willoughby Hills, OH (US)

( * ) Notice: Subject to any disclaimer, the term of this patent is extended or adjusted under 35 U.S.C. 154(b) by 0 days. days.

(21) Appl. No.: 14/679,053

(22) Filed: Apr. 6, 2015

(65) Prior Publication Data
US 2016/0287291 A1   Oct. 6, 2016

(51) Int. Cl.
*A61B 17/70*   (2006.01)

(52) U.S. Cl.
CPC ........ *A61B 17/7019* (2013.01); *A61B 17/701* (2013.01); *A61B 17/7005* (2013.01); *A61B 17/7032* (2013.01); *A61B 17/7035* (2013.01)

(58) Field of Classification Search
CPC ............ A61B 17/7004; A61B 17/7005; A61B 17/701; A61B 17/7034
USPC ................................ 606/254, 255, 261, 264
See application file for complete search history.

(56) References Cited

U.S. PATENT DOCUMENTS

| | | | |
|---|---|---|---|
| 5,092,866 A | 3/1992 | Breard et al. | |
| 6,554,831 B1 | 4/2003 | Rivard et al. | |
| 6,986,771 B2 | 1/2006 | Paul et al. | |
| 8,123,783 B2 | 2/2012 | Lins | |
| 8,267,943 B2 | 9/2012 | Ferree | |
| 2001/0027319 A1 | 10/2001 | Ferree | |
| 2003/0191470 A1 | 10/2003 | Ritland | |
| 2005/0085813 A1 | 4/2005 | Spitler et al. | |
| 2005/0203516 A1* | 9/2005 | Biedermann | A61B 17/701 606/267 |
| 2005/0277920 A1* | 12/2005 | Slivka | A61B 17/7044 606/263 |
| 2007/0191841 A1* | 8/2007 | Justis | A61B 17/701 606/250 |
| 2008/0269805 A1* | 10/2008 | Dekutoski | A61B 17/7004 606/279 |
| 2008/0294195 A1 | 11/2008 | Egli et al. | |

(Continued)

FOREIGN PATENT DOCUMENTS

EP   0322334   6/1989

OTHER PUBLICATIONS

Yazici, et al.; Fusionless instrument systems for congenital scoliosis: expandable spinal rods and vertical expandable prosthetic titanium rib in the management of congenital spine deformities in the growing child. Oct. 29, 2013.

*Primary Examiner* — Nicholas Plionis
(74) *Attorney, Agent, or Firm* — Thompson Hine LLP

(57) ABSTRACT

An orthopedic implant system is disclosed for use in correcting or reducing the progression of scoliosis. The orthopedic implant system can be inserted laterally or posteriorly and comprises an elongated flexible member secured to a user's spinal column via a plurality of vertebral body screws. Typically, the height of the elongated flexible member is significantly greater than the width, creating a flattened cross-sectional aspect. The vertebral body screws comprise a screw base and a screw head with a slot sized to accept an insert. Typically, the elongated flexible member is positioned within the slot via the insert, and is allowed to slide within the screw head as needed, as the user moves. However, at the apex of the user's scoliosis curve, the elongated flexible member is fixed within a vertebral body screw head.

20 Claims, 8 Drawing Sheets

(56) References Cited

U.S. PATENT DOCUMENTS

| | | | |
|---|---|---|---|
| 2009/0005817 A1* | 1/2009 | Friedrich | A61B 17/7007 606/246 |
| 2009/0248075 A1* | 10/2009 | Ogilvie | A61B 17/7005 606/246 |
| 2010/0042155 A1* | 2/2010 | Biedermann | A61B 17/7004 606/254 |
| 2010/0160968 A1 | 6/2010 | Josh et al. | |
| 2011/0029018 A1 | 2/2011 | Carlos | |
| 2013/0190821 A1 | 7/2013 | Marik et al. | |
| 2013/0253587 A1 | 9/2013 | Carls et al. | |

\* cited by examiner

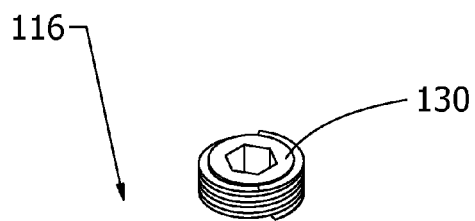
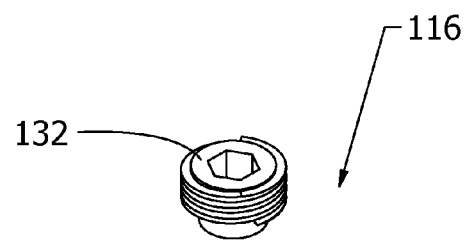
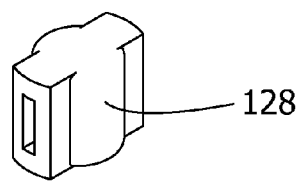
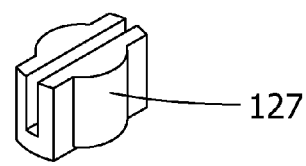
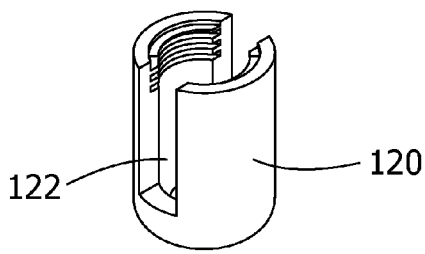
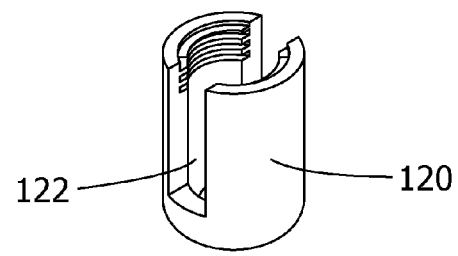
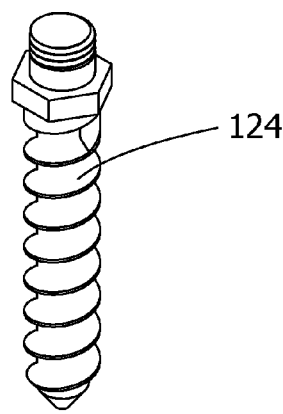
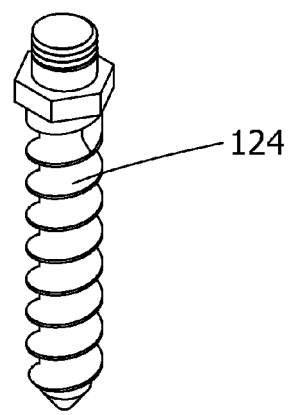
FIG. 4A    FIG. 4B

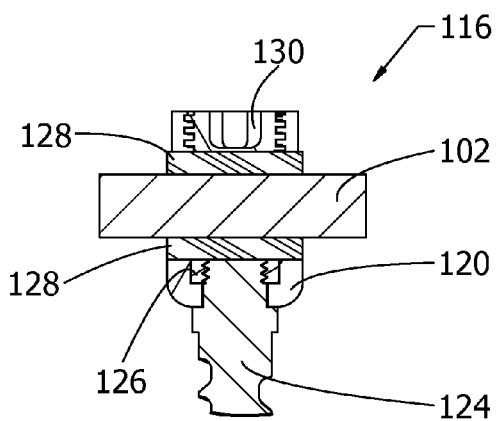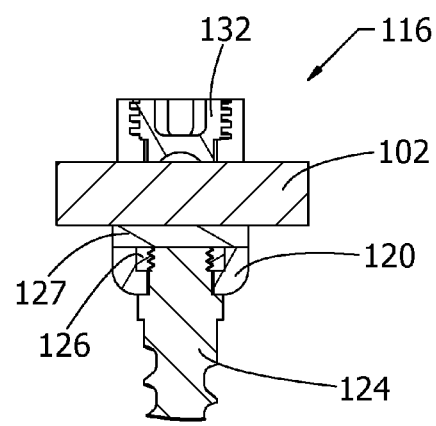
FIG. 8A            FIG. 8B
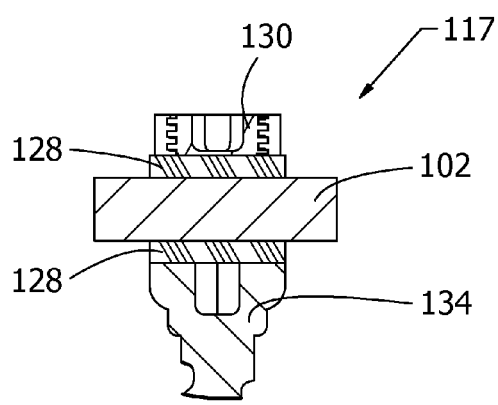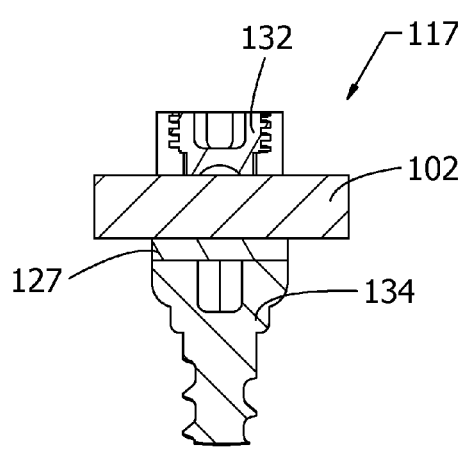
FIG. 8C            FIG. 8D

DISC AND MOTION PRESERVING IMPLANT SYSTEM

BACKGROUND

Currently, operative methods for treating spinal deformities, such as scoliosis, include correction of the spinal curvature via some form of internal fixation device, and immobilization of the spine in the corrected state. Typically, the internal fixation device includes an implantable rod or a pair of implantable rods for mounting on either side of the posterior aspect of the spinal column. When a pair of implantable rods are used, rigid transverse bars are often used to connect the rods together in spaced-apart parallel arrangement. Anchors in the form of hooks or screws are provided along each rod for anchoring the same to selected vertebrae. Once installed, the anchors are rigidly locked to the associated rod to prevent relative motion there between. Further, the arrangement may be supplemented with bone grafts and the fusion of several vertebrae in order to prevent the apparatus from breaking due to the load induced thereon. However, immobilization of the spine results in physical restrictions in movement and may cause complications throughout the patient's life. Typically, present technology for scoliosis systems immobilizes the spinal column, may not preserve a user's spinal discs, and results in physical restrictions for life that may also result in psychological issues. Thus, an effective solution is necessary.

The present invention allows a significant degree of motion in most planes while the implants are in place and unrestricted freedom of movement should the implants be removed. The flat shape of the elongated flexible member (or band) allows a user to flex, extend, or rotate while at the same time restricts lateral bending/movement at the levels of implantation. Thus, the present invention provides resistance in the plane of a scoliotic curve while at the same time allowing movement in other planes. A variation of the present invention provides the ability to correct and/or restrict vertebral rotational misalignment. Thus, the orthopedic implant system corrects scoliotic curves and/or restricts growth of scoliosis curves, while allowing preservation of the user's intervertebral discs, preservation of flexion, extension and rotational motion, the ability to modify the shape and dimensions of the band to vary the flexibility/stiffness in multiple orientations or directions depending on the user, the elimination of posterior muscle disruption, the ability of the user to grow while the disc and motion preserving implant system is in place, and the potential to remove the device after the user reaches skeletal maturity, such that a user can then live a life that does not include an immobilized spine. Thus, the orthopedic implant system benefits anyone with a spinal deformity.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises an orthopedic implant system for use in correcting or inhibiting the progression of a scoliosis curve. The orthopedic implant system comprises an elongated flexible member secured to a user's spinal column via a plurality of vertebral body screws. Typically, the height of the elongated flexible member is significantly greater than the width, creating a flattened cross-sectional aspect. Further, many configurations of the elongated flexible member are possible depending on the degree and direction of control needed including rotational control and/or correction.

The vertebral body screws comprise a typical screw base with threads and a screw head with a slot sized to accept the elongated flexible member or to accept an insert with a slot sized to accept the elongated flexible member. The vertebral body screws can be either rotational head screws or fixed head screws. Typically, a fixed head screw is used at the apex of the scoliosis curve of the user's spinal column while rotational head screws are used above and below the apex. Typically a locking end cap is used at the apex of the scoliosis curve to lock the band in place to prevent migration of the elongated flexible member. Typically, for the other screw locations, the elongated flexible member is allowed to slide within the screw heads or within an insert in the screw heads as needed, as the user moves. Further, the screw head of the rotational head screws can rotate as needed relative to the screw base, reducing stresses on the screws and the elongated flexible member as the user's spinal column extends, flexes, or rotates.

Additionally, the orthopedic implant system can be implanted laterally, via an anterior, oblique, or a lateral surgical approach, or posteriorly, depending on the wants and needs of a user. The orthopedic implant system can be designed in multiple configurations, only some of which are shown in this application.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

FIG. 4A illustrates an exploded view of a rotational head screw with a standard insert and a standard end cap in accordance with the disclosed architecture.

FIG. 4B illustrates an exploded view of a rotational head screw with a locking insert and a locking end cap in accordance with the disclosed architecture.

FIG. 8A illustrates a section view of a rotational head screw with a standard insert and end cap in accordance with the disclosed architecture.

FIG. 8B illustrates a section view of a rotational head screw with a locking insert and end cap in accordance with the disclosed architecture.

FIG. 8C illustrates a section view of a fixed head screw with a standard insert and end cap in accordance with the disclosed architecture.

FIG. 8D illustrates a section view of a fixed head screw with a locking insert and end cap in accordance with the disclosed architecture.

DESCRIPTION OF PREFERRED EMBODIMENTS

Figure 1:
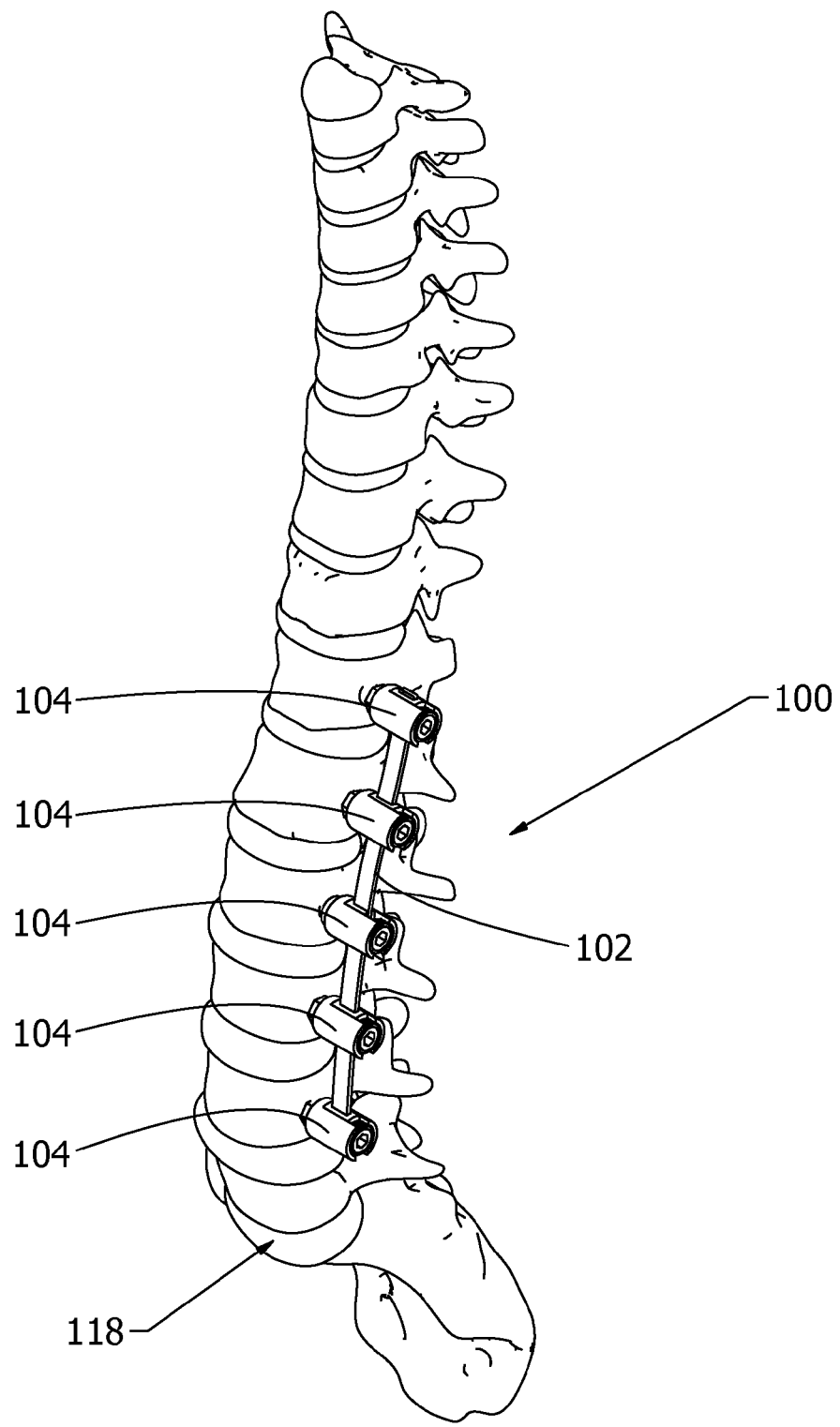
FIG. 1 illustrates a perspective view of the orthopedic implant system secured to a spine in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Furthermore, for clarity, the drawings of the devices are slightly enlarged vs. the vertebral bodies.

The present invention allows a significant degree of motion in most planes while the implants are in place and unrestricted freedom of movement should the implants be removed after the user reaches skeletal maturity. The flat shape of the elongated flexible member (or band) allows a user to flex, extend, or rotate while at the same time restricts lateral bending/movement at the levels of the implantation. Thus, the orthopedic implant system provides resistance to the scoliotic curve at the index levels while at the same time allowing movement in other planes. A variation of the present invention provides the ability to correct and/or restrict vertebral rotational misalignment. Thus, the orthopedic implant system corrects and/or restricts the growth of scoliosis curves, while allowing preservation of the user's intervertebral disc, preservation of flexion, extension and rotational movements, the ability to modify the shape of the band to vary the flexibility in multiple orientations or directions depending on the user, and the potential to remove the device after the user reaches skeletal maturity, such that a user may then live a life that does not include an immobilized spine. Thus, the orthopedic implant system benefits anyone with a spinal deformity.

The surgical approach for the orthopedic implant system may be anterior, lateral, oblique or posterior and the system may be implanted posteriorly (not detailed or shown) or laterally and comprises an elongated flexible member secured to a user's spinal column via a plurality of vertebral body screws. The preferred embodiment is lateral to the spine and the height of the elongated flexible member is oriented parallel to or in the same plane as the long axis of the screw. For a posterior system (not shown) the screws would be inserted posteriorly and angled as needed to allow sufficient fixation to or in the pedicles, and the sidesurfaces of the elongated flexible member would be oriented in a manner other than parallel to the long axis of the screw body (system not shown).

Typically, the height of the elongated flexible member is significantly greater than the width or thickness, creating a flattened cross-sectional, aspect. For example, the ratio of height to width (or thickness), can range from approximately 3:1 to approximately 20:1 depending on the needs of the user, the curvature of the spine and the material used.

Figure 2:
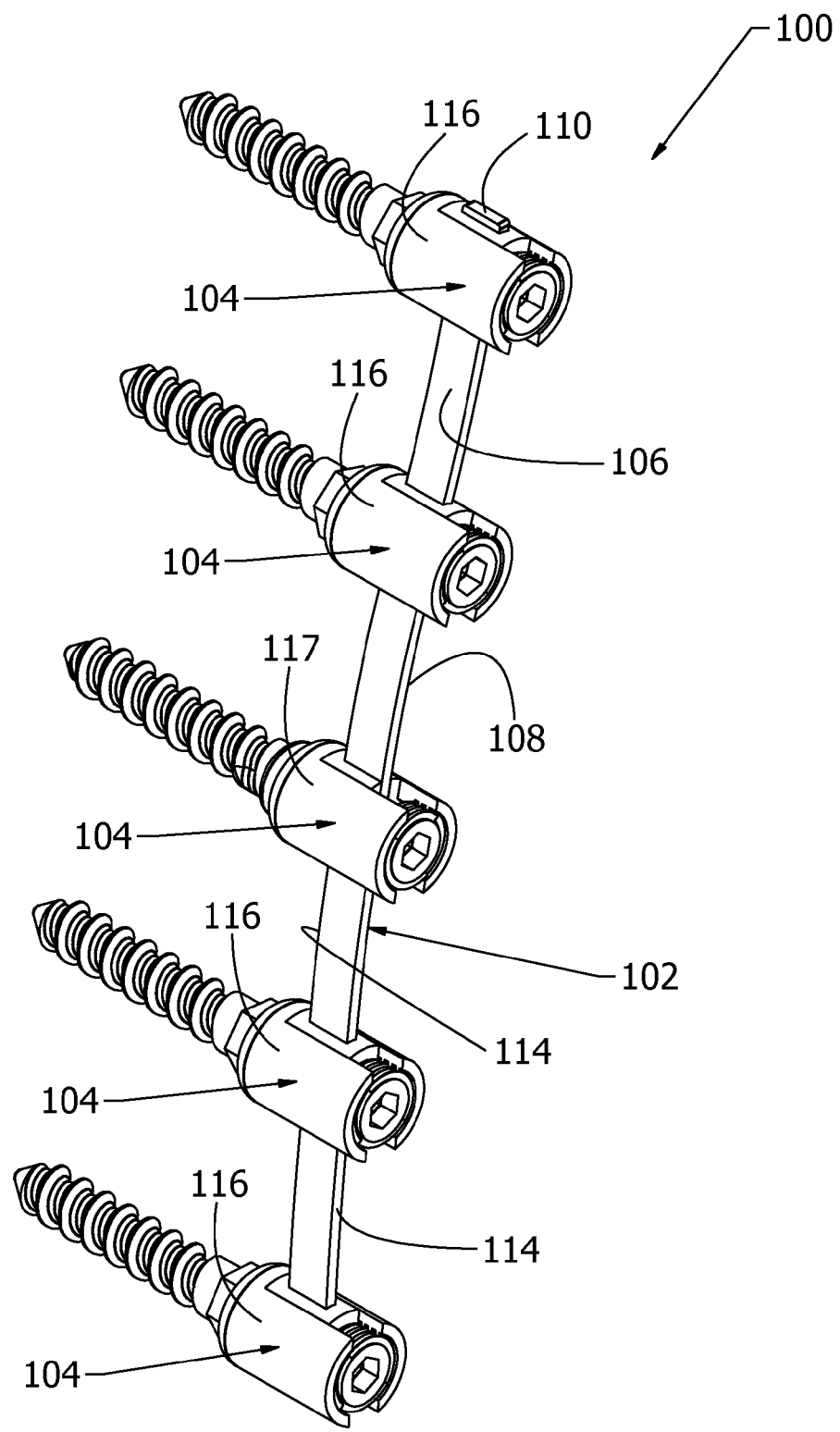
FIG. 2 illustrates a perspective view of the orthopedic implant system in accordance with the disclosed architecture.
Figure 3:
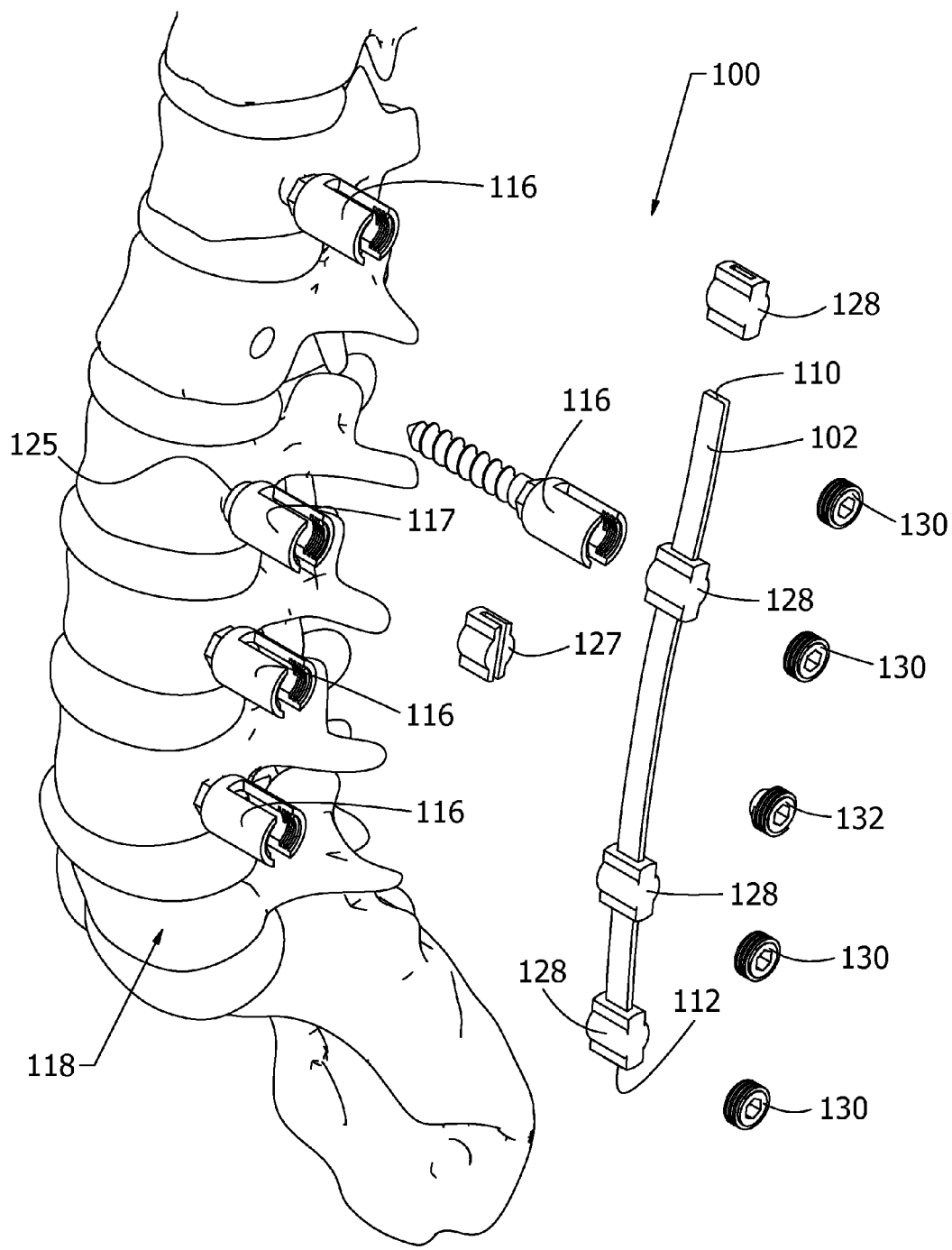
FIG. 3 illustrates an exploded view of the orthopedic implant system secured to a spine in accordance with the disclosed architecture.
Figures 5A, 5B:
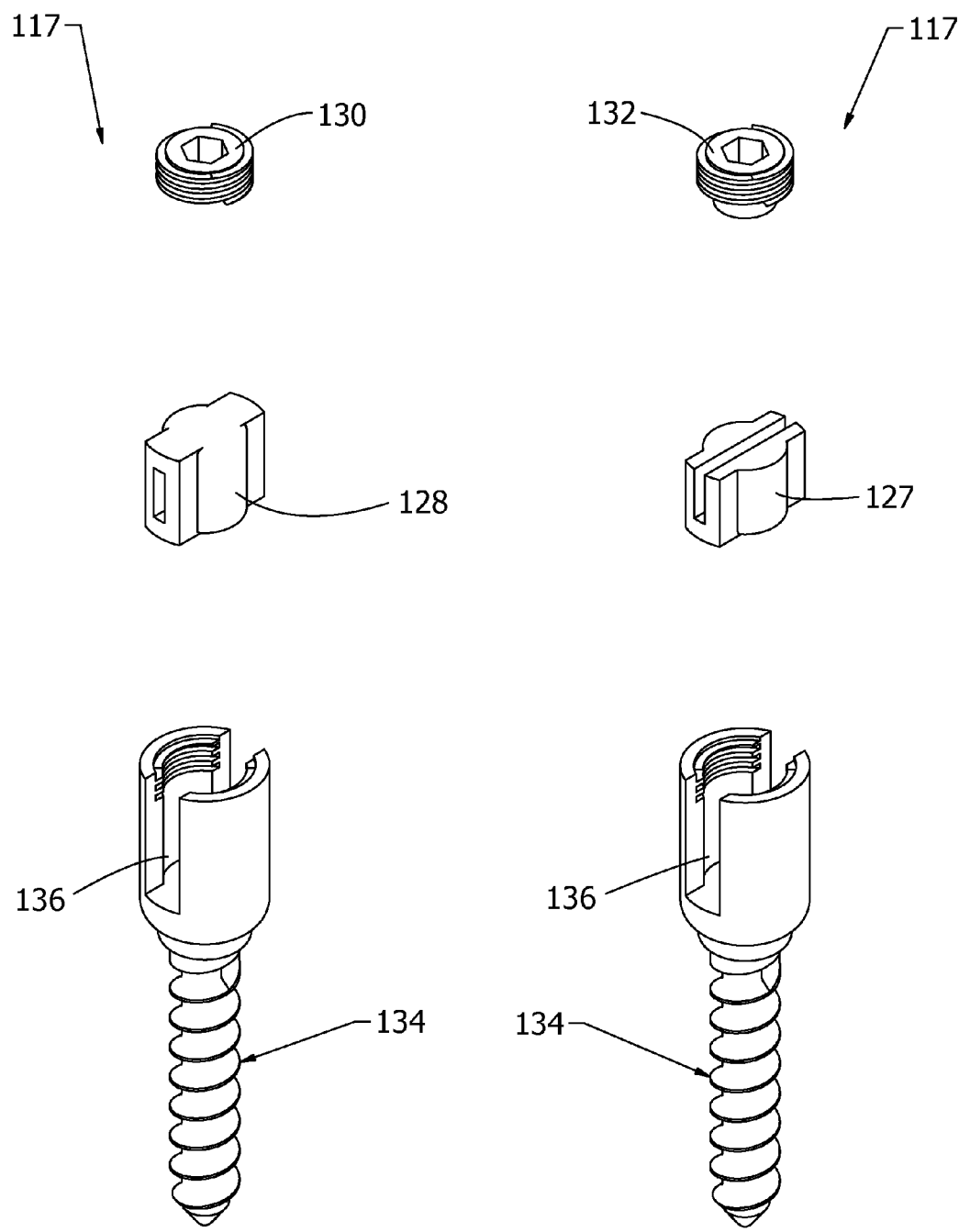
FIG. 5A illustrates an exploded view of a fixed head screw with a standard insert and a standard end cap in accordance with the disclosed architecture.
FIG. 5B illustrates an exploded view of a fixed head screw with a locking insert and a locking end cap in accordance with the disclosed architecture.

Referring initially to the drawings, FIGS. 1-3 illustrate the orthopedic implant system 100 for use in correcting or maintaining a scoliosis curve. The orthopedic implant system 100 comprises an elongated flexible member 102 secured to a user's spinal column via a plurality of vertebral body screws 104 (as shown in FIG. 1).

The elongated flexible member 102 comprises a top surface 106, a bottom surface 108, a first end 110, a second end 112, and opposing sides 114. Typically, the height, top and bottom surfaces 106 and 108, of the elongated flexible member 102 is significantly greater than the width, opposing sides 114, creating a flattened cross-sectional aspect, but the elongated flexible member 102 can be any suitable shape as is known in the art. Further, many configurations of the elongated flexible member 102 are possible depending on the degree and direction of control needed, including rotational control of the vertebral bodies of the user's spinal column, and best design to optimize the system's potential and to minimize debris generation and potential breakage.

Figure 7A:
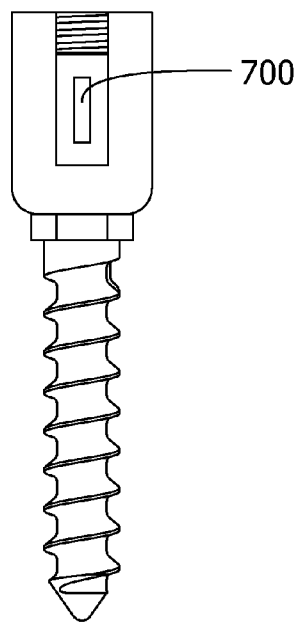
FIG. 7A illustrates an end view of the band and insert in a rotational head screw in accordance with the disclosed architecture.
Figure 7B:
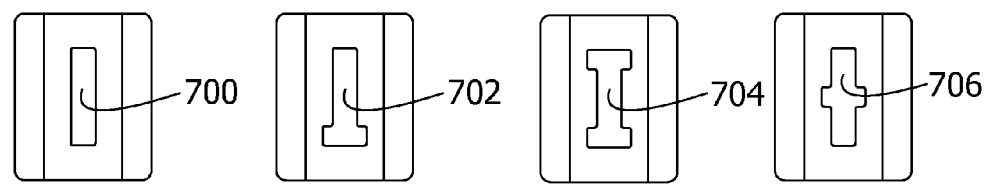
FIG. 7B illustrates an end view of the inserts showing multiple configurations of the insert and the band that passes through the insert within the orthopedic implant system in accordance with the disclosed architecture.
Figure 7B:
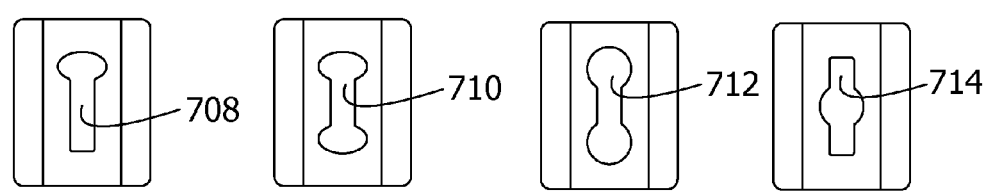

For example FIGS. 7A-B show some of the end on configurations 110 and/or 112 of the flexible member 102; standard flat sided band 700, a partial I-beam shape 702, a full I-beam shape 704, a cross-sectional I-beam shape 706, a partial barbell shape 708, a full barbell shape 710 or 712, and a cross-sectional barbell shape 714. In addition the elongated flexible member 102, as viewed from the side 106, can include multiple different configurations (not shown) including a straight flat band, a curved band, a stepped band, or a tapered band. Thus, there is a potential to develop elongated flexible members 102 that have different/varying thickness and different cross sectional geometries, and can be tapered or stepped in various dimensions such as thickness, width, etc. Additionally, the elongated flexible member 102 can have additional configurations to optimize system potential and enable varying degrees of response to the need for overall control of a patient's rotational or flexion/extension movements. Further, the ends 110 and/or 112 of the elongated flexible member 102 can extend past an end of the vertebral body screw heads 104 to allow for growth in the spinal column or an extended range of motion.

The elongated flexible member 102 would generally be constructed of titanium, cobalt chromium and/or stainless steel, etc., though any other suitable material may be used to manufacture the elongated flexible member 102 as is known in the art without affecting the overall concept of the invention. Further, the corners or other geometries of the elongated flexible member 102 can be rounded or radiused to eliminate any sharp edges.

While the shape and size of the elongated flexible member 102 may vary greatly depending on the wants and needs of a user, and depending on the severity of a curve of the user's spine (scoliosis curve), the elongated flexible member 102 is approximately between 3 and 12 inches in length as measured from a first end 110 to a second end 112, and approximately between 0.5 millimeters and 5 millimeters thick as measured from a top surface 106 to a bottom surface 108, and approximately between 3 and 20 millimeters thick as measured from opposing sides 114.

Furthermore, the orthopedic implant system 100 comprises a plurality of vertebral body screws 104 which are engageable with the elongated flexible member 102 and which anchor the elongated flexible member 102 to a user's spinal column 118. The vertebral body screws 104 can be any suitable bi-cortical or uni-cortical bone screws as is known in the art, as long as the screws can be inserted into the vertebra of a user's spine and secured. Further, the vertebral body screws 104 could be rotational head screws 116 or fixed head screws 117, depending on the needs of the user. The vertebral body screws 104 would generally be constructed of titanium, cobalt chromium, stainless steel, etc., though any other suitable material may be used to manufacture the vertebral body screws 104 as is known in the art without affecting the overall concept of the invention. Any suitable number of vertebral body screws 104 can be used as is known in the art, and per the user's wants and needs. Further, implant system 100 could be placed on either the convex or concave side of the scoliosis curve or both.

The vertebral body screws comprise a screw head, with either a slot sized to accept an elongated flexible member or an insert with a slot sized to accept an elongated flexible member, and a screw base. Typically, both rotational head screws 116 and fixed head screws 117 are used to anchor the elongated flexible member 102. Although fixed head and rotational head screws and locking and non-locking inserts and end caps may be used interchangeably as determined by the surgeon, in a typical construct, a fixed head screw 117 may be used along with a locking insert 127 and a locking end cap 132 at the apex 125 of the scoliosis curve of the user's spinal column 118 to prevent migration of the elongated flexible member 102. Rotational head screws 116 with standard inserts 128 and standard end caps 130 are then used above and below the apex 125 to allow the elongated flexible member 102 to slide as needed post implantation and the screw head 120 of the rotational head screws to rotate as needed relative to the screw base 124, reducing forces and tension on the elongated flexible member 102, the screw head 120, the inserts, and the screw base 124 as the user's spinal column 118 extends, flexes and rotates.

As shown in FIGS. 4A-B and FIGS. 8A-B, the rotational head screws 116 comprise a screw base 124 and a screw head 120 with a slot 122 sized to accept insert 127 or 128. The screw head 120 is placed on the screw base 124 and then a locking nut (or retaining nut) 126 is placed onto the screw head 120 and threaded into position. The locking nut 126 locks into position on the screw head 120 and holds the screw head 120 on the screw base 124 but still allows it to rotate as needed, as the user moves. An insert (127 or 128) is then inserted into the screw head 120 for retaining the elongated flexible member 102. The insert can be a standard insert 128 which fully encapsulates the elongated flexible member 102 and allows it to move or slide as needed. Then a standard end cap 130 is secured onto the screw head 120 to secure the standard insert 128 in place. Typically, the elongated flexible member 102 is positioned within the slot of the standard insert 128, and is allowed to slide within the screw head 120 as needed, as the user moves. Further, the screw head 120 rotates as needed relative to the screw base 124, allowing the elongated flexible member 102 to extend, flex and rotate, as the user's spinal column 118 extends, flexes and rotates. Furthermore, instead of a standard insert 128, a locking insert 127 can be used which surrounds only the bottom and sides of the elongated flexible member 102. A locking end cap 132 with a protrusion is then threaded onto the insert 127 till it contacts the elongated flexible member 102, holding the member 102 in place. Additionally, the rotational head screws 116 positioned at the superior and inferior tips of the elongated flexible member 102 may be larger than standard screw heads to cover the end tips of the flexible member 102.

Typically, the elongated flexible member 102 is fixed within a fixed head screw 117 at an apex 125 of a scoliosis curve of the user's spinal column 118. However, instead of the apex 125 of the scoliosis curve, the elongated flexible member 102 can be fixed within a fixed head screw 117 at both the first end 110 and the second end 112 of the elongated flexible member 102, or any other suitable position as is known in the art. As shown in FIGS. 5A-B and FIGS. 8C-D, the fixed head screws 117 comprise a one piece screw 134 with a slot 136 sized to accept the elongated flexible member 102. An insert (127 or 128) is then inserted into the screw 134 for retaining the elongated flexible member 102. The insert can be a standard insert 128 which fully encapsulates the elongated flexible member 102 and allows it to move or slide as needed. Then a standard end cap 130 is secured onto the screw head 134 to secure the standard insert 128 in place. Typically, the elongated flexible member 102 is positioned within the slot of the standard insert 128, and is allowed to slide within the screw 134 as needed, as the user moves. Furthermore, instead of a standard insert 128, a locking insert 127 can be used which surrounds only the bottom and sides of the elongated flexible member 102. A locking end cap 132 with a protrusion is then threaded onto the insert 127 till it contacts the elongated flexible member 102, holding the member 102 in place.

Typically, during the surgical procedure, after the screws are placed, an elongated flexible member 102 is positioned into an insert (127 or 128) sized and shaped to accept the type of elongated flexible member chosen by the surgeon, some examples of which are 700, 702, 704, 706, 708, 710, 712 and 714 (as shown in FIG. 7B). The assembly is then inserted into the space in the screw head 122 or 136. The insert can be a standard insert 128 which fully encapsulates the elongated flexible member 102 while still allowing the elongated flexible member 102 to move or slide as needed post implantation, as the user moves. A standard end cap 130 is then inserted into the screw head to secure the standard insert 128 in place. Furthermore, instead of a standard insert 128, a locking insert 127 can be used which surrounds only the bottom and sides of the elongated flexible member 102. A locking end cap 132 is then inserted into the screw head until the inferior protrusion of the end cap compresses the elongated flexible member 102, fixing the member 102 in place. Further, for rotational head screws 116 the screw head 120 rotates as needed relative to the screw base 124, allowing the elongated flexible member 102 to more easily extend, flex and rotate, as the user's spinal column 118 extends, flexes and rotates reducing forces on the screw head 120, screw base 124, insert 127 or 128, and elongated flexible member 102. Additionally, the screws positioned at the superior and inferior tips of the elongated flexible member 102 may be larger (not shown) than standard screw heads to cover the end tips 110 and/or 112 of the flexible member 102.

Additionally, the orthopedic implant system 100 can be implanted laterally or posteriorly, depending on the wants and needs of a user. The orthopedic implant system 100 can be designed in multiple configurations, only some of which are shown in this application. For example, the plurality of vertebral body screws 104 can anchor a first elongated flexible member 102 along a lateral side of the user's spinal column 118. Then, a second plurality of vertebral body screws 104 can anchor a second elongated flexible member 102 to the opposing side of the user's spinal column 118 at the same or another curve location. Further, there is a possibility that the orthopedic implant system 100 can be removed after the user reaches skeletal maturity which provides the potential for a user to achieve a more normal degree of spinal function post removal.

Figure 6:
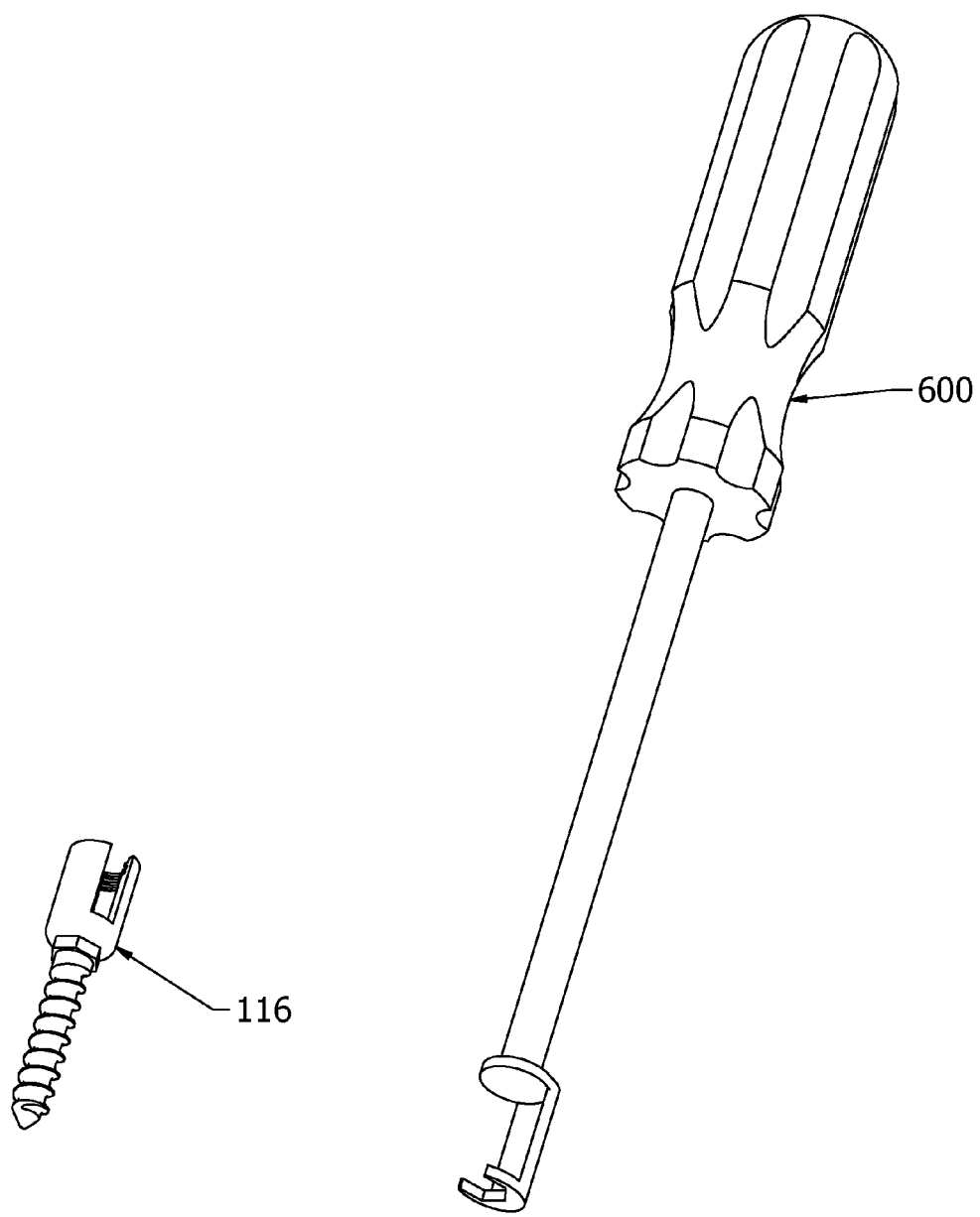
FIG. 6 illustrates a perspective view of a driver for inserting the rotational head screws in accordance with the disclosed architecture.

FIG. 6 illustrates a driver device 600 that can be used to implant the rotational head screws 116, a prior art orthopedic hex head screwdriver (not shown) would be used for the fixed head screws 117. In operation, a surgeon (not shown) would choose the specific size and/or shape of the elongated flexible member 102 that meets their users' needs and/or wants, depending on the size, flexibility, rotation, and/or curvature of the user's spinal column 118 the orthopedic implant system 100 will be used with. The surgeon would then determine if the orthopedic implant system 100 would be implanted laterally or posteriorly in the user. Once the position is determined, the surgeon would make an incision in the user and then would move soft tissue out of the approach area as needed. The surgeon would prepare the site for each vertebral body screw 104 and would insert as many vertebral body screws 104 as needed (i.e., rotational 116 and/or fixed 117 head screws), and spanning as many levels as necessary.

Once the vertebral body screws 104 are in place and secure, the surgeon will thread the chosen elongated flexible member 102 into the proper number of associated inserts 128 or 127. Then the surgeon, at the apex 125 of the user's scoliosis curve, secures (or fixes) the elongated flexible member 102 within a screw head using a locking insert 127 and a locking end cap 132, preventing migration of the elongated flexible member 102. The surgeon then uses an instrument (persuader) with a specially shaped tip (not shown) to straighten the spine. The base of the persuader is set on the head of the screw at the apex of the curve, the surgeon then places the end of the persuader under the head on the next screw and applies force, bringing the vertebral body in line with the apex vertebral body. The surgeon then sets the end cap (130 or 132). Once done, the surgeon moves to the next vertebral body screw 104 and repeats until all vertebral bodies, above and below the apex, are in line and end caps (130 or 132) set.

Thus, the elongated flexible member 102 is fixed in position at the apex 125 of the user's scoliosis curve, but can slide within the screw heads 120 or inserts 128 at the screws positioned superior or inferior to the apex 125 of the user's scoliosis curve. Accordingly, the orthopedic implant system 100 allows the user to flex, extend, or rotate while at the same time correcting a scoliosis curve and/or restricting its growth. Furthermore, after the user reaches skeletal maturity, the orthopedic implant system 100 can potentially be removed, allowing a user to live a life that does not include an immobilized spine.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An orthopedic implant system for use in correcting scoliosis curves, comprising:
   a plurality of vertebral body screws each comprising a screw base and a screw head with a slot for accepting an insert;
   an elongated, elastically bendable beam engageable with the plurality of vertebral body screws via such inserts, the elastically bendable beam having unequal principal flexural rigidities so as to preferentially resist bending in a plane of a scoliosis curve; and
   a plurality of such inserts including at least one locking insert, the locking insert having a locking end cap threadable into the screw head of a respective one of the vertebral body screws to contact and hold the elongated, elastically bendable beam in place within the locking insert, and at least one non-locking insert, the non-locking insert having a non-locking end cap threadable into the screw head of a respective one of the vertebral body screws to contact an insert wall surrounding the elongated, elastically bendable beam while allowing the elongated, elastically bendable beam to freely slide within the non-locking insert;
   whereupon in an assembly of the plurality of vertebral body screws, the beam, and the plurality of inserts, the one of the plurality of vertebral body screws engaged with the beam via the at least one non-locking insert is freely movable along the beam, with respect to the one of the plurality of vertebral body screws engaged with the beam via the at least one locking insert, without resistance from intervening structure.

2. The orthopedic implant system of claim 1, wherein the elongated, elastically bendable beam has a ratio of height to thickness ranging from 3:1 to 20:1, and wherein the larger aspect of the elongated, elastically bendable beam is positionable within each insert parallel to a long axis of each screw base.

3. The orthopedic implant system of claim 1, wherein the plurality of vertebral body screws are configured to anchor the elongated, elastically bendable beam along a lateral side of a user's spinal column.

4. The orthopedic implant system of claim 3, further comprising a second plurality of vertebral body screws configured to anchor a second such elongated, elastically bendable beam to an opposing side of the user's spinal column via such inserts, the second elongated, elastically bendable beam, and a second plurality of such inserts.

5. The orthopedic implant system of claim 1, wherein the plurality of vertebral body screws includes at least one fixed head screw configured to accept the locking insert.

6. The orthopedic implant system of claim 5, wherein the plurality of vertebral body screws includes at least one rotational head screw configured to accept the non-locking insert.

7. The orthopedic implant system of claim 6, wherein the screw head of the rotational head screw is configured to cover an end tip of the elongated, elastically bendable beam.

8. The orthopedic implant system of claim 6, wherein an end tip of the elongated, elastically bendable beam is extendable through and past both the slot of the rotational head screw and an accepted non-locking insert to allow for growth in the spinal column or an extended range of motion.

9. An orthopedic implant device for use in correcting a scoliosis curve, comprising:
a plurality of vertebral body screws each comprising a screw base and a screw head with a slot for accepting an insert;
an elongated, elastically bendable beam engaged with the plurality of vertebral body screws via such inserts, the elastically bendable beam having unequal principal flexural rigidities so as to preferentially resist bending in a plane of a scoliosis curve; and
a plurality of such inserts wherein at least one of the plurality of such inserts is a locking insert accepted within one of the plurality of vertebral body screws, the locking insert having a locking end cap threaded into the screw head of the one of the plurality of vertebral body screws so as to contact and hold the elongated, elastically bendable beam in place within the locking insert, and at least two of the plurality of such inserts are non-locking inserts accepted within other ones of the plurality of vertebral body screws, each non-locking insert having a non-locking end cap threaded into the screw head of one of the other ones of the plurality of vertebral body screws so as to engage a wall surrounding the elongated, elastically bendable beam while allowing the elongated, elastically bendable beam to slide within the non-locking insert as needed,
whereupon the other ones of the plurality of vertebral body screws are freely movable along the beam, with respect to the one of the plurality of vertebral body screws, without resistance from intervening structure.

10. The orthopedic implant device of claim 9, wherein the elongated, elastically bendable beam has a ratio of height to thickness ranging from 3:1 to 20:1 and wherein the larger aspect of the elongated, elastically bendable beam is positioned within each insert parallel to the slot of each screw head.

11. The orthopedic implant device of claim 9, wherein the plurality of vertebral body screws are configured to anchor the elongated, elastically bendable beam along a lateral side of a user's spinal column.

12. The orthopedic implant device of claim 9, wherein the elongated, elastically bendable beam is fixed within the locking insert and the locking insert is disposed between non-locking inserts.

13. The orthopedic implant device of claim 12, wherein the elongated, elastically bendable beam is slidable within non-locking inserts disposed proximate to the end tips of the elongated, elastically bendable beam.

14. The orthopedic implant device of claim 13, wherein the screw heads of the vertebral body screws associated with the non-locking inserts disposed proximate the end tips of the elongated, elastically bendable beam are configured to cover the end tips of the elongated, elastically bendable beam.

15. The orthopedic implant device of claim 13, where the end tips of the elongated, elastically bendable beam extend through and past both the non-locking inserts disposed proximate the end tips of the elongated, elastically bendable beam and the slots of the vertebral body screws associated therewith.

16. An orthopedic implant system for use in correcting scoliosis curves, comprising:
a plurality of vertebral body screws each comprising a screw base and a screw head with a slot;
an elongated, elastically bendable beam engageable with the plurality of vertebral body screws via the slots, the elastically bendable beam having unequal principal flexural rigidities so as to preferentially resist bending in a plane of a scoliosis curve; and
a plurality of end caps including at least one locking end cap threadable into the screw head of a respective one of the vertebral body screws to contact and hold the elongated, elastically bendable beam in place within the screw head, and at least one non-locking end cap threadable into the screw head of a respective one of the vertebral body screws to close the slot while allowing the elongated, elastically bendable beam to slide within the slot as needed;
whereupon in an assembly of the plurality of vertebral body screws, the beam, and the plurality of end caps, the one of the plurality of vertebral body screws closed by the at least one non-locking end cap is freely movable along the beam, with respect to the one of the plurality of vertebral body screws holding the beam via the at least one locking end cap, without resistance from intervening structure.

17. The orthopedic implant system of claim 16, wherein the elongated, elastically bendable beam has a ratio of height to thickness ranging from 3:1 to 20:1, and wherein the larger aspect of the elongated, elastically bendable beam is positionable within each slot parallel to a long axis of each screw base.

18. The orthopedic implant system of claim 16, wherein the plurality of vertebral body screws are configured to anchor the elongated, elastically bendable beam along a lateral side of a user's spinal column.

19. The orthopedic implant system of claim 16, wherein the plurality of vertebral body screws includes at least one fixed head screw configured to accept the locking end cap.

20. The orthopedic implant system of claim 16, wherein the plurality of vertebral body screws includes at least one rotational head screw configured to accept the non-locking end cap.

* * * * *